(12) United States Patent
Williams et al.

(10) Patent No.: US 8,771,720 B2
(45) Date of Patent: *Jul. 8, 2014

(54) MEDICAL DEVICE COMPRISING POLYHYDROXYALKANOATE HAVING PYROGEN REMOVED USING OXIDIZING AGENT

(75) Inventors: Simon F. Williams, Sherborn, MA (US); David P. Martin, Arlington, MA (US); Tillman Gerngross, Hanover, NH (US); Daniel M. Horowitz, Alexandria, VA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,663

(22) Filed: Jul. 10, 2012

(65) Prior Publication Data
US 2012/0328523 A1 Dec. 27, 2012

Related U.S. Application Data

(60) Division of application No. 13/021,419, filed on Feb. 4, 2011, now Pat. No. 8,231,889, which is a continuation of application No. 11/748,723, filed on May 15, 2007, now Pat. No. 7,906,135, which is a continuation of application No. 10/642,926, filed on Aug. 18, 2003, now Pat. No. 6,949,568, which is a division of application No. 09/819,447, filed on Mar. 28, 2001, now Pat. No. 6,623,749, which is a division of application No. 09/076,198, filed on May 12, 1998, now Pat. No. 6,245,537.

(60) Provisional application No. 60/046,211, filed on May 12, 1997, provisional application No. 60/054,289, filed on Jul. 31, 1997, provisional application No. 60/063,501, filed on Oct. 24, 1997, provisional application No. 60/065,921, filed on Nov. 17, 1997.

(51) Int. Cl.
| | | |
|---|---|---|
| A61F 2/00 | (2006.01) | |
| A61F 2/02 | (2006.01) | |
| A61F 13/00 | (2006.01) | |
| C12P 7/62 | (2006.01) | |
| C12P 1/04 | (2006.01) | |
| C12N 11/08 | (2006.01) | |
| C12N 11/04 | (2006.01) | |
| C12N 5/07 | (2010.01) | |
| C07K 17/04 | (2006.01) | |
| C07K 17/08 | (2006.01) | |

(52) U.S. Cl.
USPC ........... 424/423; 424/422; 424/443; 424/486; 424/93.7; 435/135; 435/170; 435/180; 435/182; 435/395; 530/815; 530/817

(58) Field of Classification Search
CPC ............... A61F 2/00; A61F 2/02; A61F 2/04; A61F 13/00; C12P 1/04; C12N 11/08; C12N 11/04; C12N 5/06; C12K 17/00; C12Q 1/00; C12M 1/00
See application file for complete search history.

(56) References Cited

U.S. PATENT DOCUMENTS

| | | | | |
|---|---|---|---|---|
| 4,648,978 A | * | 3/1987 | Makinen et al. | 210/759 |
| 4,711,241 A | | 12/1987 | Lehmann | |
| 4,910,145 A | * | 3/1990 | Holmes et al. | 435/259 |
| 5,026,381 A | | 6/1991 | Li | |
| 5,245,023 A | | 9/1993 | Peoples | |
| 5,250,430 A | | 10/1993 | Peoples | |
| 5,334,698 A | | 8/1994 | Witholt | |
| 5,480,394 A | | 1/1996 | Ishikawa | |
| 5,480,794 A | | 1/1996 | Peoples | |
| 5,512,669 A | | 4/1996 | Peoples | |
| 5,516,565 A | * | 5/1996 | Matsumoto | 428/35.7 |
| 5,534,432 A | | 7/1996 | Peoples | |
| 5,563,239 A | | 10/1996 | Hubbs | |
| 5,584,885 A | | 12/1996 | Seckel | |
| 5,688,900 A | * | 11/1997 | Cooper et al. | 528/301 |
| 5,735,863 A | | 4/1998 | DellaValle | |
| 5,842,477 A | * | 12/1998 | Naughton et al. | 128/898 |
| 6,245,537 B1 | | 6/2001 | Williams | |
| 6,420,273 B1 | | 7/2002 | Lin | |
| 6,610,764 B1 | | 8/2003 | Martin | |

(Continued)

FOREIGN PATENT DOCUMENTS

| | | |
|---|---|---|
| EP | 0258781 | 3/1988 |
| EP | 0628586 | 12/1994 |

(Continued)

OTHER PUBLICATIONS

Gagnon et al., Polymer, vol. 35, 1994, pp. 4358-4367.*
Agostini, at al., "Synthesis and Characterization of Poly-β-Hydroxybutyrate. I. Synthesis of Crystalline DL Poly-β-Hydroxybutyrate from DL-β-Butyrolactone," Polym. Sci., Part A-1, 9:2775-87 (1971).
Akhtar, "Physiomechanical Properties of bacterial P(HB-HV) Polyesters and Their Uses in drug Delivery," The British Library Document Supply Centre, UMI, (1990).

(Continued)

Primary Examiner — David M Naff
(74) Attorney, Agent, or Firm — Pabst Patent Group LLP

(57) ABSTRACT

Polyhydroxyalkanoates (PHAs) from which pyrogen has been removed are provided. PHAs which have been chemically modified to enhance physical and/or chemical properties, for targeting or to modify biodegradability or clearance by the reticuloendothelial system (RES), are described. Methods for depyrogenating PHA polymers prepared by bacterial fermentation processes are also provided, wherein pyrogens are removed from the polymers without adversely impacting the polymers' inherent chemical structures and physical properties. PHAs with advantageous processing characteristics, including low melting points and/or solubility in non-toxic solvents, are also described. The PHAs are suitable for use in in vivo applications such as in tissue coatings, stents, sutures, tubing, bone, other prostheses, bone or tissue cements, tissue regeneration devices, wound dressings, drug delivery, and for diagnostic and prophylactic uses.

16 Claims, No Drawings

(56) References Cited

U.S. PATENT DOCUMENTS

| | | | |
|---|---|---|---|
| 6,623,749 B2* | 9/2003 | Williams et al. | 424/423 |
| 7,244,442 B2 | 7/2007 | Williams | |
| 7,906,135 B2* | 3/2011 | Williams et al. | 424/423 |
| 2007/0131930 A1 | 6/2007 | Aida | |
| 2007/0296052 A1 | 12/2007 | Lee | |

FOREIGN PATENT DOCUMENTS

| | | | |
|---|---|---|---|
| EP | 0754467 | | 1/1997 |
| JP | 07275344 | | 10/1995 |
| WO | 9851812 | | 11/1988 |
| WO | 9600263 | | 1/1996 |
| WO | WO 96/24682 | * | 8/1996 |
| WO | 9707153 | | 2/1997 |
| WO | 9848028 | | 10/1998 |
| WO | 9932536 | | 7/1999 |

OTHER PUBLICATIONS

Anderson, et al., "Occurrence, Metabolism, metabolic Role, and Industrial Uses of bacterial Polyhydroxyalkanoates," Microbiological Reviews pp. 450-472 (1990).
Berger, et al., "PHB recovery by hypochlorite digestion of non-PHB biomass", Biotechnonology Techniques, 3(4):227-232 (1989).
Byrom, "Miscellaneous Biomaterials," in Biomaterials (D. Byrom, ed.) pp. 333-359 (MacMillan Publishers, London 1991).
Clavijo-Alvarez, et al. "Comparison of biodegradable conduits within aged rat sciatic nerve defects," Plast Reconstr Surg. 119(6):1839-51(2007).
Conti, B. et al., "Use of polylactic acid for the preparation of microparticulate drug delivery systems," J. Microencapsulation 9:153-166 (1992).
Cookson, "It grows on trees," Financial Times p. 6 (Aug. 12, 1992).
De Smet, et al., "Characterization of intracellular inclusions formed by *Pseudomonas oleovorans* during growth on octane," J. Bacteriol. 154:870-78 (1983).
Dubois, et al., "Macromolecular Engineering of Polylactones and Polylactides. 12. Study of the Depolymerization Reactions of Poly(-caprolactone) with Functional Aluminum Alkoxide End Groups," Macromolecules 26:4407-12 (1993).
Gagnon, et al, "A thermoplastic elastomer produced by the bacterium *Pseudomonas oleovarans*," Rubber World 207:32-38 (1992).
Gross, et al., "β-Monosubstituted-β-propiolactones Using Trialkylaluminum-Water Catalytic Systems and Polymer Characterization," Macromolecules 21:2657-68 (1988).
Hocking, "Biopolyesters" in Chemistry and Technology of Biodegradable Polymers, (G.J.L. Griffin, ed.) pp. 48-96 (Chapman and Hall, London 1994).
Hocking, at al., R.H., "Syndiotactic poly[(R,S)-β-hydroxybutyrate] isolated from methyaluminum-catalyzed polymerization," Polym. Bull. 30:163-70 (1993).
Holmes, P.A., "Biologically Produced (R)-3-hydroxyalkanoate Polymers and Copolymers," in D.C. Bassett Ed., "Developments in Crystalline Polymers," Elsevier, London, vol. 2, 1988, pp. 1-65.
Hori, et al., "Ring-Opening Copolymerization of Optically Active β-Butyrolactone with Several Lactones Catalyzed by Distannoxane Complexes: Synthesis of New Biodegradable Polyesters," Macromolecules 26:4388-90 (1993).
Hori, et al., "Ring-Opening Polymerization of optically Active β-Butyrolactone Using Distannoxane Catalysts: Synthesis of High Molecular Wright Poly(3-hydroxybutyrate)," Macromolecules 26:5533-34 (1993).
Horsch, "Inheritance of Functional Foreign Genes in Plants" Science 223:49-498 (1984).
Huijberts, et al., "*Pseudomonas putida* KT2442 cultivated on glucose accumulates poly (3-hydroxyalkanoates) consisting of saturated and unsaturated monomers", Appl Environ Microbiol., 58(2):536-44 (1992).
Keeler, "Don\t Let Food Go to Waste—Make Plastic Out of It," R&D Magazine pp. 52-57 (1991).

Keeler, "Plastics Grown in Bacteria Inch Toward the Market," R&D Magazine pp. 46-52 (1991).
Kemnitzer, J.E. et al., "Preparation of predominantly Syndiotactic Poly(β-hydroxybutyrate) by the Tributylin Methoxide Catalyzed Ring-Opening Polymerization of racemic β-Butyrolactone," Macromolecules 26:1221-29 (1993).
Kishida, et al. "Formulation assisted biodegradeable polymer matrices" Chemical and Pharmaceutical Bulletin, JP Pharm Society of Japan. 37 (7):1954-1956(1989).
Koosha, "Preparation and characterization of biodegradable polymeric drug carriers," Ph.D. Dissertation, 1989, Univ. Nottingham, UK., Diss. Abstr. Int. B 51:1206 (1990).
Lafferty, et al., "Microbial Production of Poly-b-hydroxybutyric acid," H.J. Rehm and G. Reed, Eds., "Biotechnology", Verlagsgesellschaft, Weinheim, vol. 66, 1988, pp. 135-176.
Le Borgne, et al., "Stereoselective polymerization of β-bytyrolactone," Polymer 30:2312-19 (1989).
Lemoigne and Roukhelman, "Fermetation β-Hydroxybutyrique Caracterisation et Evolution Des Produits de Deshydration et de Polymerisation de L\acide β-Dehydroxybutyrique," Annales des fermentations, 5:527-36 (1925).
Lloyd, et al. "Transformation of *Arabidopsis thalania* with *Agrobacterium tumefaciens*," Science 234: 464-466 (1986).
Mathiowitz & Langer, "Polyanhydride microspheres as drug delivery systems," M. Donbrow Ed., in Microcapsules Nanopart. Med. Pharm. CRC, Boca Raton, Florida, 1992, Ch. 5, pp. 99-123.
Maysinger, "Microencapsulation and the Grafting of Genetically Transformed Cells as Therapeutic Strategies to rescue Degenerating Neurons of the CNS," Reviews in the Neurosciences 6:15-33 (1995).
McMillin, "Elastomers for Biomedical Applications," Rubber Chem. Technol. 67:417-46 (1994).
McWilliams, "Plastics as High as an Elephant\s Eye?" Business Week pp. 110-111 (Aug. 19, 1991).
Müller, et al., "Poly(hydroxyalkanoates): A Fifth Class of Physiologically Important Organic Biopolymers," Angew. Chem. Int. Ed. Engl. 32:477-502 (1993).
Ogawa, Y. et al., "A New Technique to Efficiently Entrap Leuprolide Acetate into Microcapsules of Poly Lactic Acid or Copoly(Lactic/Glycolic) Acid," Chem. Pharm. Bull. 36:1095-103 (1988).
Peoples, et al., "Poly- -hydroxybutyrate Biosynthesis in *Alcaligenes eutrophus* H16," J. Biol. Chem 264(26):15293-15297 (1989).
Peoples, et al., "Polyhydroxybutyrate (PHB): A Model System for Biopolymer Engineering: II," Dawes, ed. in Novel Biodegradable Microbial Polymers Kluwer Academic Publishers, Netherlands, 1990, pp. 191-202.
Pinto, "Hydrogen Peroxide as depyrogenation agent for medical devices components", Revista De Saude Publica, 29(1):75-79 (1995).
Poirier, et al., "Progress Toward Biologically Produced Biodegradable thermoplastics," Adv. Mater. 5(1):30-37 (1993).
Poirier, "Perspectives on the production of polyhydroxyalkanoates in plants," FEMS Microbiology Reviews 103:237-246 (1992).
Pool, "In Search of the Plastic Potato," Science 245:1187-1189 (1989).
Schlosshauer, "Synthetic nerve guide implants in humans: a comprehensive survey." Neurosurgery 59:740-748 (2006).
Steinbüchel,. "Polyhydroxyalkanoic Acids," in D. Byrom Ed., "Biomaterials", MacMillan Publishers, London, 1991, pp. 123213.
Steinbüchel, et al., "Molecular basis for biosynthesis and accumulation of polyhydroxyalkanoic acids in bacteria," FEMS Microbiology Reviews 103:217-230 (1992).
Steinbüchel, et al., "A Pseudomonas strain accumulating polyesters of 3-hydroxybutyric acid and medium-chain-length 3-hydroxyalkanoic acids," Appl. Microbiol. Biotechnol. 37:691-97 (1992).
Steinbüchel and Valentin, "Diversity of bacterial polyhydroxyalkanoic acids," FEMS Microbiol., Lett. 128:219-28 (1995).
Tanahashi, et al., "Thermal Properties and Stereoregularity of Poly(3-hydroxybutyrate) Prepared from optically Active β-Butyrolactone with a Zinc-Based Catalyst," Macromolecules 24:5732-33 (1991).

(56) References Cited

OTHER PUBLICATIONS

Wallen and Rohwedder, "Poly-β-hydroxyalakaonate from Activated Sludge," Environ. Sci. Technol. 8:576-79 (1974).

Williams, et al., "Biodegradable plastics from plants," Chemtech 26:38-44 (1996).

Xie, W. et al., "Ring-opening Polymerization of β-butyrolactone by Thermophilic Lipases," Macromolecules 30:6997-98 (1997).

* cited by examiner

MEDICAL DEVICE COMPRISING POLYHYDROXYALKANOATE HAVING PYROGEN REMOVED USING OXIDIZING AGENT

CROSS-REFERENCE TO RELATED APPLICATIONS

This application is a divisional of U.S. Ser. No. 13/021,419, filed Feb. 4, 2011 entitled, "Polyhydroxyalkanoates for In Vivo Applications", by Simon F. Williams, David P. Martin, Tillman Gerngross, and Daniel M. Horowitz, now U.S. Pat. No. 8,231,889, which is continuation application of U.S. Ser. No. 11/748,723, filed May 15, 2007, now U.S. Pat. No. 7,906,135, which is a continuation application of U.S. Ser. No. 10/642,026, filed Aug. 15, 2003, now U.S. Pat. No. 7,244,442, which is a divisional application of U.S. Ser. No. 09/819,447, filed Mar. 28, 2001, now U.S. Pat. No. 6,623,749, which is a divisional application of U.S. Ser. No. 09/076,198, filed May 12, 1998, now U.S. Pat. No. 6,245,537, which claims priority to U.S. Ser. No. 60/046,211, entitled "Biocompatible Polyhydroxyalkanoates" filed May 12, 1997 by Simon F. Williams; U.S. Ser. No. 60/054,289, entitled "Derivatization of PHAs for Biomedical Applications" filed Jul. 31, 1997, by David Martin; U.S. Ser. No. 60/063,501, entitled "Polyhydroxyalkanoate Stents" filed Oct. 24, 1997, by Simon F. Williams and David P. Martin; and U.S. Ser. No. 60/065,921, entitled "Method for Making Biocompatible Polyhydroxyalkanoates" filed Nov. 17, 1997, by Simon F. Williams and David P. Martin; the disclosures of these applications are incorporated herein by reference.

BACKGROUND OF THE INVENTION

The present application is generally directed to polyhydroxyalkanoates polymers and methods of preparation to remove pyrogen and use thereof in a variety of biomedical applications, including tissue engineering, wound dressings, drug delivery, and in prosthetics.

Polyhydroxyalkanoates (PHAs) are polymers with repeating hydroxy acid monomeric units. PHAs have been reviewed in several publications, including Byrom, "Miscellaneous Biomaterials," in *Biomaterials* (D. Byrom, ed.) pp. 333-59 (MacMillan Publishers, London 1991); Hocking and Marchessault, "Biopolyesters" in *Chemistry and Technology of Biodegradable Polymers* (G. J. L. Griffin, ed.) pp. 48-96 (Chapman and Hall, London 1994); Müller and Seebach, *Angew. Chem. Int. Ed. Engl.*, 32:477-502 (1993); Steinbüchel, "Polyhydroxyalkanoic Acids," in *Biomaterials* (D. Byrom, ed.) pp. 123-213 (MacMillan Publishers, London 1991); and Williams and Peoples, *CHEMTECH*, 26:38-44 (1996).

Polyhydroxybutyrate (PHB) and polyhydroxybutyrate-hydroxyvalerate (PHBV) have been used commercially as a biodegradable replacement for synthetic commodity resins, and have been extensively studied for use in biomedical applications. Examples of these biomedical applications include controlled release (Pouton and Akhtar, *Adv. Drug Delivery Rev.*, 18:133-62 (1996)), tablet formulations, surgical sutures, wound dressings, lubricating powders, blood vessels, tissue scaffolds, surgical implants to join tubular body parts, bone fracture fixation plates, and other orthopedic uses, (Hocking and Marchessault, "Biopolyesters" in *Chemistry and Technology of Biodegradable Polymers*, (G. J. L. Griffin, ed.) pp. 48-96 (Chapman and Hall, London 1994) and references therein); European Patent Application 754 467 A1 (Bowald, et al.). See also Saghir Akhtar, Ph.D. Thesis for the University of Bath, 1990, "Physicomechanical Properties of Bacterial P(HB-HV) Polyesters and Their Uses in Drug Delivery". PHBV has been used to sustain cell growth and in tissue reconstruction (see, e.g., Rivard, et al., *J. Appl. Biomat.*, 6:65-68 (1995)). However, PHBs and PHBVs have been shown to induce acute inflammatory responses when implanted in vivo (Akhtar at pp. 50-51, and references cited therein).

Biodegradable polymers for medical uses must be biocompatible and degrade into non-toxic metabolites. Medical devices must also be nonpyrogenic, i.e., the products must not produce fever reactions when administered to patients. The presence of bacterial endotoxin (which is an integral component of the outer cell surface of Gram-negative bacteria), in the product is by far the largest concern of manufacturers in achieving nonpyrogenation. (Weary and Pearson, *BioPharm.*, 1:22-29 (1988)). The U.S. Food and Drug Administration (FDA), for example, requires the endotoxin content of medical devices not exceed 20 U.S. Pharmacopeia (USP) endotoxin units (EU) per device, except for those devices that contact the cerebrospinal fluid, where the content must not exceed 2.15 USP endotoxin units per device. Acceptable endotoxin levels may need to be even lower for some applications, where the polymer is to be used for particularly sensitive applications. Therefore, in developing PHAs for use in medical devices, the materials must meet the specific requirements set for endotoxin content, particularly for PHAs derived by fermentation of gram-negative bacteria, where the polymers are exposed to large amounts of endotoxin in the cell culture.

U.S. Pat. No. 5,334,698 to Witholt, et al. discloses sutures, films, skin grafts, and bone grafts prepared from an optically active polyester isolated from *Pseudomonas oleovorans* cells. PCT Application Publication WO 96/00263 (Eggink, et al.) discloses an aqueous latex-like PHA dispersion, wherein the PHA includes saturated or unsaturated 3-hydroxy fatty acids having a carbon chain length of 6-14. Hocking and Marchessault, "Biopolyesters" in *Chemistry and Technology of Biodegradable Polymers*, (G. J. L. Griffin, ed.) pp. 48-96 (Chapman and Hall, London 1994) also discloses polyesters with functionalized side-chains prepared by bacteria upon modifying the feed substrate, and their use for preparing drug delivery systems. These materials would inherently include endotoxin, and there is no disclosure of any methods for removing endotoxins or procedures for providing depyrogenated polymers suitable for in vivo medical use.

Despite the large amount of literature describing production, purification, and applications development of PHAs, there are currently no reported methods specifically for depyrogenating PHA polymers. PHAs have a relatively high affinity for endotoxins, complicating the use of routine procedures for depyrogenation. Thus, there is a need to develop methods for depyrogenating PHA polymers, particularly when they are produced by fermentation in Gram-negative bacteria.

Even aside from the issue of pyrogenicity, there remains a need to develop additional biodegradable polymers for in vivo use, particularly polymers with alternative physical and chemical properties. These properties include characteristics relevant to ease of processing, as well as suitability for the end use. An important physical property for processing of the polymers is the melting point or glass transition temperature of the materials. PHB, PHBV (0-24% V), PGA and PLGA, for example, all melt only at relatively high temperatures, above 136° C. This high temperature can be a disadvantage in fabrication if the polymers are to be combined in the melt with other heat sensitive components. It would be advantageous to have a class of PHAs which have melting points or glass transition temperatures below 136° C. for use in biomedical applications. Further, many PHAs are only soluble in potentially toxic chlorinated solvents. There is thus a need to develop low melting PHAs that can be melt processed at low temperatures and/or can be dissolved in non-toxic, generally acceptable solvents. However, there is currently no commercial source for polyhydroxyalkanoate materials with these properties.

Other properties such as the thermal and mechanical properties, density and crystallinity, are also of interest. These properties can be modified by mixing or blending PHAs with other materials, or by changing the PHA composition. The commercially available PHAs, PHB and PHBV, have only limited uses. Other PHAs can be used for very different applications. For example, the extension-to-break of PHBV ranges from about 8 to 42%, whereas the same property for polyhydroxyoctanoate (PHO), a low melting PHA, is about 380% (Gagnon, et al., *Rubber World*, 207:32-38 (1992)). Similarly, PHBV has a Young's Modulus of between 1,000 and 3,500 MPa and a tensile strength of between 20 and 31 MPa, in contrast to PHO which has a Young's Modulus of 8 MPa and a tensile strength of 9 MPa (Gagnon, et al., *Rubber World*, 207:32-38 (1992)). These properties and others have lead to PHO being classified as a thermoplastic elastomer (Gagnon, et al., *Rubber World*, 207:32-38 (1992)). The covalent crosslinking of unsaturated pendant groups of several polyhydroxyalkanoate thermoplastic elastomers has been reported (Gagnon, et al., *Polymer*, 35:4358-67 (1994)), although the use of the polymers for preparing medical devices is not disclosed. It would be useful to develop biocompatible low melting PHAs containing groups which can be covalently modified, or which can be subsequently modified to expose functional groups which can be derivatized, for use in preparing medical devices.

Accordingly, it is an object of this invention to provide polyhydroxyalkanoate polymers having most of pyrogen removed, for use in biomedical applications.

It is another object of this invention to provide biocompatible polyhydroxyalkanoate polymers with low melting points and/or solubility in non-toxic, non-halogenated solvents.

It is another object of this invention to provide polyhydroxyalkanoates having desirable properties for use in a variety of biomedical applications, such as drug delivery, tissue engineering, medical imaging, and the manufacture of prosthetics, stents, and coatings.

It is a further object of this invention to provide methods for making biomedical devices using polyhydroxyalkanoate polymers.

SUMMARY OF THE INVENTION

Polyhydroxyalkanoates (PHAs) from which pyrogen has been removed are provided for use in numerous biomedical applications. PHAs which have been chemically modified to enhance physical and/or chemical properties, for targeting or to modify biodegradability or clearance by the reticuloendothelial system (RES), are described. Methods for depyrogenating PHA polymers prepared by bacterial fermentation processes are also provided, wherein pyrogens are removed from the polymers without adversely impacting the polymers' inherent chemical structures and physical properties. PHAs with advantageous processing characteristics, including low melting points and/or solubility in non-toxic solvents, are also described. PHAs are provided which are suitable for use in in vivo applications such as in tissue coatings, stents, sutures, tubing, bone and other prostheses, bone or tissue cements, tissue regeneration devices, wound dressings, drug delivery, and for diagnostic and prophylactic uses. Properties which are selected for include degradability, elasticity, inclusion of functional groups or derivatized groups, which can in turn be used to attach targeting agents, and bioadhesion.

DETAILED DESCRIPTION OF THE INVENTION

Biocompatible polyhydroxyalkanoates (PHAs) are provided wherein pyrogens such as endotoxin, present due to the process by which the PHAs are made, are removed without damage to the polymer composition or structure. In a preferred embodiment, the polymers have melting points or glass transition temperatures less than 136° C., and/or are soluble in non-toxic non-halogenated solvents.

I. Polyhydroxyalkanoates

Several types of polyhydroxy alkanoates are formed in nature by various organisms in response to environmental stress. These PHAs can be broadly divided into three groups according to the length of their pendant groups and their respective biosynthetic pathways. Relatively short pendant groups are the $C_{3-5}$ hydroxy acids, whereas relatively long pendant groups are $C_{6-14}$ hydroxy acids.

There are three major types of naturally occurring PHAs. The first type includes only relatively short hydroxy acid monomeric units. The second type include both relatively short and relatively long hydroxy acid monomeric units. The third type includes only relatively long hydroxy acid monomeric units. Those with short pendant groups, such as polyhydroxybutyrate (PHB), a homopolymer of R-3-hydroxybutyric acid (R-3HB) units, are highly crystalline thermoplastic materials (Lemoigne and Roukhelman, *Annales des fermentations*, 5:527-36 (1925)). PHAs containing the short R-3HB units randomly polymerized with much longer pendant group hydroxy acid units were first reported in the early seventies (Wallen and Rohwedder, *Environ. Sci. Technol.*, 8:576-79 (1974)). A number of microorganisms which specifically produce copolymers of R-3HB with these longer pendant group hydroxy acid units are also known and belong to this second group (Steinbüchel and Wiese, *Appl. Microbial. Biotechnol.*, 37:691-97 (1992)). In the early 1980's, a research group in The Netherlands identified the third group of PHAs, which contains predominantly longer pendant group hydroxy acids (De Smet, et al., *J. Bacteria*, 154:870-78 (1983)).

PHAs may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes: thiolase, reductase, and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization. The last enzyme in this pathway, namely the synthase, has a substrate specificity that can accommodate $C_{3-5}$ monomeric units, including R-4-hydroxy acid and R-5-hydroxy acid units. This biosynthetic pathway is found, for example, in the bacteria *Zoogloea ramigera* and *Alcaligenes eutrophus*.

The biosynthetic pathway which is used to make the third group of PHAs, long pendant group polyhydroxyalkanoates (LPGPHAs), is still partly unknown. However, it is currently thought that the monomeric hydroxyacyl units leading to the LPGPHAs are derived by the α-oxidation of fatty acids and the fatty acid pathway. The R-3-hydroxyacyl-Coenzyme substrates resulting from these routes are then polymerized by PHA synthases (sometimes called polymerases) that have substrate specificities favoring the larger monomeric units in the $C_{6-14}$ range. LPGPHAs are produced, for example, by *Pseudomonads*.

The second group of PHAs containing both short R-3HB units and longer pendant group monomers are believed to utilize both the pathways to provide the hydroxy acid monomers. The latter are then polymerized by PHA synthases able to accept these units.

Roughly 100 different types of PHAs have been produced by fermentation methods so far (Steinbüchel and Valentin, *FEMS Microbiol., Lett.*, 128:219-28 (1995)). A number of these PHAs contain functionalized pendant groups such as esters, double bonds, alkoxy, aromatic, halogens, and hydroxy groups. Transgenic systems for producing PHAs in both microorganism and plants, as well as enzymatic methods for PHA synthesis, are reviewed by Williams and Peoples, *CHEMTECH*, 26:38-44 (1996).

Two PHAs belonging to the first group, polyhydroxybutyrate (PHB) and polyhydroxybutyrate-co-valerate (PHBV), have been extensively studied. PHBV is a copolymer of R-3HB units with 5-24% R-3-hydroxyvaleric acid (R-3HV), and is known commercially as Biopol™ (supplied by ICI/Zeneca). These polymers are natural thermoplastics which can be processed using conventional polymer technology and which have industrially useful properties, such as biodegradability in soil and marine environments and good barrier properties. They are characterized by melting points which range from 130 to 180° C., and extensions-to-break of 8 to 42% (see Zeneca Promotional Literature, Billingham, UK 1993).

1. Polymer Formulas

The PHAs as described herein can be in the form of homopolymers, block copolymers, or random copolymers. Biocompatible polymers are generally defined as those polymers that result in minimal tissue reaction when implanted in vascularized tissue. As used herein, biocompatible polymers are those which do not elicit an acute inflammatory response when implanted into the muscle of an animal such as a mouse.

In some embodiments, the polymers can also be characterized as having low endotoxin levels. Preferably, the PHAs are highly pure materials, with purities exceeding 95%, more preferably exceeding 98%. The PHAs may be purified by extraction with or precipitation from aqueous solutions, organic solvents, supercritical fluids, or combinations thereof.

The molecular weight of the polymers is preferably between 300 and $10^7$, and, more preferably, between 10,000 and 10,000,000 Daltons. The PHAs preferably contain one or more units, more preferably between 10 and 100,000 and most preferably between 100 and 30,000 units of the following formula:

        FORMULA I wherein n is an integer, for example, between one and 15, preferably between one and four; and wherein $R^1$, $R^2$, $R^3$, and $R^4$ are independently selected from hydrogen, methyl, $C_{2-15}$ straight, branched or cyclic alkyl, alkenyl or alkynyl groups, alkaryl groups, aralkyl groups, heteroalkyl groups, heteroaryl groups, hydroxy groups, thiol groups, disulfides, ether groups, thioether groups, ester groups, carboxylic acid groups, amine groups, amide groups, halogens, nitrogen-substituted radicals; and/or oxygen-substituted radicals.

Suitable monomeric units include hydroxybutyrate, hydroxyvalerate, hydroxyhexanoate, hydroxyheptanoate, hydroxyoctanoate, hydroxynonanoate, hydroxydecanoate, hydroxyundecanoate, and hydroxydodecanoate units. PHAs including monomers and polymers and derivatives of 3-hydroxyacids, 4-hydroxyacids and 5-hydroxyacids can be used. Representative PHAs are described in Steinbüchel, A. and Valentin, H. E., *FEMS Microbiol., Lett.*, 128:219-28 (1995).

Preferred PHAs have melting points or glass transition temperatures less than 136° C. These materials are referred to as "low melting PHAs". The low melting PHAs specifically exclude the homopolymer, polyhydroxybutyrate (PHB), and the commercial copolymers of R-3-hydroxybutyric acid and R-3-hydroxyvaleric acid (PHBV) with a valerate content in the copolymer of between 0 and 24%.

Although described herein primarily with reference to the polyhydroxyalkanoate polymers, it is understood that these polymers may be blended with other polymers, and/or copolymerized with monomers or other polymers to form polyhydroxyalkanoate copolymers. Examples of other polymers particularly suited for biomedical applications include biodegradable polymers such as polyhydroxy acids prepared from polylactic acid, polyglycolic acid, and copolymers thereof, polycarbonates, polyorthoesters, polyanhydrides, polyphosphazenes, polyamino acids, proteins, and polysaccharides. The term "polyhydroxyalkanoate" refers to polyhydroxyalkanoate polymers, blends, and copolymers, unless otherwise stated.

2. Preparation of PHAs

The PHAs can be prepared from a biological source such as a microorganism which naturally produces the PHAs or which can be induced to produced the PHAs by manipulation of culture conditions and feedstocks, or microorganisms or a higher organism such as a plant, which has been genetically engineered so that it produces PHAs.

Methods which can be used for producing PHA polymers from microorganisms which naturally produce polyhydroxyalkanoates are described in U.S. Pat. No. 4,910,145 to Holmes, et al.; Byrom, D., "Miscellaneous Biomaterials," in D. Byrom, Ed., "Biomaterials" MacMillan Publishers, London, 1991, pp. 333-59; Hocking, P. J. and Marchessault, R. H. "Biopolyesters", G. J. L. Griffin, Ed., "Chemistry and Technology of Biodegradable Polymers," Chapman and Hall, London, 1994, pp. 48-96; Holmes, P. A., "Biologically Produced (R)-3-hydroxyalkanoate Polymers and Copolymers," in D. C. Bassett Ed., "Developments in Crystalline Polymers," Elsevier, London, Vol. 2, 1988, pp. 1-65; Lafferty et al., "Microbial Production of Poly-b-hydroxybutyric acid," H. J. Rehm and G. Reed, Eds., "Biotechnology", Verlagsgesellschaft, Weinheim, vol. 66, 1988, pp. 135-76; Müller and Seebach, *Angew. Chem. Int. Ed. Engl.* 32:477-502 (1993).

Methods for producing PHAs in natural or genetically engineered organisms are described by Steinbüchel, A. "Polyhydroxyalkanoic Acids," in D. Byrom Ed., "Biomaterials", MacMillan Publishers, London, 1991, pp. 123-213; Williams and Peoples, *CHEMTECH*, 26:38-44, (1996); Steinbüchel and Wiese, *Appl. Microbiol. Biotechnol.*, 37:691-97 (1992); U.S. Pat. Nos. 5,245,023; 5,250,430; 5,480,794; 5,512,669; 5,534,432 to Peoples and Sinskey; Agostini, D. E. et al., *Polym. Sci., Part A*-1, 9:2775-87 (1971); Gross, R. A. et al., *Macromolecules*, 21:2657-68 (1988); Dubois, P. I. et al., *Macromolecules*, 26:4407-12 (1993); Le Borgne, A. and Spassky, N., *Polymer*, 30:2312-19 (1989); Tanahashi, N. and Doi, Y., *Macromolecules*, 24:5732-33 (1991); Hori, Y. M. et al., *Macromolecules*, 26:4388-90 (1993); Kenmitzer, J. E. et al., *Macromolecules*, 26:1221-29 (1993); Hori, Y. M. et al., *Macromolecules*, 26:5533-34 (1993); Hocking, P. J. and Marchessault, R. H., *Polym. Bull.*, 30:163-70 (1993); Xie, W. et al., *Macromolecules*, 30:6997-98 (1997), and U.S. Pat. No. 5,563,239 to Hubbs, et al, the teachings of which are incorporated herein.

PHAs prepared using methods other than bacterial systems typically do not contain pyrogens, and, accordingly, need not be depyrogenated. Pyrogens present in bacterial fermentation systems are usually endotoxins, although other toxins may also be present, particularly in Gram positive bacterial systems, and may also be present in alternative production systems.

PHAs can also be prepared using chemical syntheses, for example, via the ring-opening polymerization of β-lactone monomers using various catalysts or initiators such as aluminoxanes, distannoxanes, or alkoxy-zinc and alkoxy-aluminum compounds (see Agostini, et al., *Polym. Sci.*, Part A-1, 9:2775-87 (1971); Gross, et al., *Macromolecules*, 21:2657-68 (1988); and Dubois, et al., *Macromolecules*, 26:4407-12 (1993)); or via condensation polymerization of esters (see, for example, U.S. Pat. No. 5,563,239 to Hubbs, et al., and references therein). Researchers also have developed chemo-enzymatic methods to prepare PHAs. For example, Xie, et al., *Macromolecules*, 30:6997-98 (1997) reported a ring opening polymerization of beta-butyrolactone by thermophilic lipases to yield PHB.

3. Modification of PHAs

The PHA polymers can contain or be modified to include other molecules, such as bioactive and detectable compounds, surface active agents, other degradable or non-degradable polymers, and materials used to modify the mechanical properties of the PHAs, such as plasticizers, fillers, and binders. The modifications can involve covalent and/or non-covalent attachment of molecules to the PHAs. The modifications may also include chemical or physical treatment of the PHAs, which may subsequently be followed by covalent or non-covalent attachment of molecules. Covalent modification of PHAs can enhance their usefulness for biomedical applications. Newly introduced functional groups may then serve as sites of covalent attachment, for example, for drugs, cell attachment peptides, and growth factors.

Functionalized PHAs are polyhydroxyalkanoates containing reactive functional groups. Reactive functional groups, such as carboxylic and amino groups, impart new properties to the polymer and provide sites for its covalent derivatization. These groups can be introduced into PHAs in a number of ways. For example, functionalized (or functionalizable) monomers may be incorporated into the PHAs during production of the polymer. Controlled fermentation conditions have been used to produce PHAs with a variety of functional groups in the pendant side chain such as alkenes, halogens, esters and branched alkyl groups. After isolation, chemical treatments can subsequently convert these functional groups into a variety of others, such as carboxylic, amino, and carbonyl groups. Tillman recently has prepared gram quantities of bromo- and alkene-functionalized PHAs.

Another approach to functionalizing PHAs is to chemically or physically modify the isolated parent (functionalized) polymer. Modification of the PHA after production, purification, and isolation is particularly attractive for a number of reasons. Fermentation systems for the production of unfunctionalized PHAs are typically the easiest, cheapest, and highest yielding, since this obviates the need for expensive functionalized monomers. Purification of the unfunctionalized polymer is not complicated by the presence of functional groups. The degree of polymer modification can be controlled in a derivatization procedure after the polymer is isolated and purified.

The polyester backbone of a PHA is a potential site for modification through aminolysis or transesterification reactions. These reactions can be performed on the bulk polymer, or directed selectively to the surface of a PHA article. Surface modification has the significant advantage in that only the surface of the material is modified, while bulk modification of the polymer results in a uniformly modified material. Modifications that cleave the polyester backbone are expected to cause random chain scission, and, depending upon the level of polymer modification, should result in a significant reduction of the polymer MW. As an example of this approach, PHO films have been modified with bioactive molecules, such as biotin; to produce surfaces which bind streptavadin-HRP conjugates (see Example 17 which follows).

The pendant side group is also a potential site for modification of PHAs. Chemical or physical treatments that generate reactive species, such as free radicals, will modify the pendant side chain. While attack of the polymer backbone may also occur, conditions for the selective modification of the pendant side chain should be achievable. Gas plasma treatment is an example of this type of modification. Depending on the type of gas used to generate the plasma, this type of treatment can introduce a variety of new functional groups.

Gas plasma is an ionized form of gas, which is typically associated with extremely high temperatures. Hot gas plasma, for instance, is formed on the sun as the result of nuclear fusion. However, cold gas plasma can be formed at low temperatures using low pressure conditions and the right type of energy. Fluorescent lights are an example. It is this type of gas plasma which is useful for the modification of PHAs. The energy used to create the plasma, such as radio frequency power or electrical discharge, strips electrons from the gas, producing free electrons, gas ions, and excited molecules. When the electrons recombine with the ions and excited molecules, a glowing "plasma" is produced. Even though the ions and excited molecules may have a very high degree of kinetic energy (and thus a high temperature), the temperature of the bulk gas is relatively low (near room temperature). These "excited" ions and molecules impact the surface, fragmenting its molecular structure. Recombination events alter the surface at the molecular level, thereby forming new chemical bonds and introducing new functional groups. The type of functional group (e.g., amino, carboxyl, carbonyl, sulfonate, fluorine, or hydroxyl) that results depends upon the nature of the plasma gas and the conditions of the treatment.

The PHAs can be treated with a chemical reagent to cleave ester linkages in the polymer backbone. This results in the formation of free hydroxyl and carboxylic acid groups which alter the charge on the polymer as well as provides reactive functional groups for subsequent modification and attachment of molecules. The treatment also can promote or reduce cellular adhesion by, or cell and tissue growth on, the polymer. Reagents which can be used to cleave the polymer backbone include water, bases, acids, nucleophiles, electrophiles, plasma, and metal ions. Hydrolysis of the esters can also be performed enzymatically using esterases. The polymers can also be cleaved by irradiation and/or application of heat.

These modifications can be carried out homogeneously in solution. However, if the polymer is in a solid form (e.g., particles or a film), then such modifications may be limited primarily to the polymer surface. This method allows surface properties to be modified without altering the overall mechanical properties of the underlying polymer or, accordingly, devices formed of the polymers.

Certain PHAs with functional pendant groups can also be modified by chemical and physical means. Such modifications may change polymer properties, for example, or allow subsequent attachment of other molecules or cells. The exact modifications that can be made vary according to the nature of the functional group and will be apparent to those skilled in the art. For example, functional pendant groups like esters can be converted to acids, and unsaturated groups can be oxidized to diols, alcohols, aldehydes, and acids. Reagents for modifying functional pendant groups can readily be selected by those skilled in the art.

Bioactive species can also be attached to the ends of the polymers, either covalently or ionically, or by mixing the bioactive species with the polymeric material. Coupling chemistry involving hydroxyl and carboxyl end groups or other reactive groups which can be present on the molecules is well known to those skilled in the art.

The PHAs can also be modified non-covalently. For example, the PHAs include a carboxylic acid group, which can form a ionic bond with amine groups present on materials such as proteins and peptides, polylysine, and other cationic materials. Such modifications can, for example, change surface properties like hydrophobicity and surface charge of the polymers. Examples of molecules which can modify PHAs non-covalently are surface active agents and lipids.

4. Surface Modification of PHAs

Surface modifications, which introduce new functional groups, allow for the selective attachment of specific bioactive agents. After production, isolation, and purification of the PHA, the chemical surface treatment or gas plasma treatment conditions can be controlled to vary the level of modification. It is also possible to prepare surface modification gradients, which allow for the preparation of concentration gradients of bioactive compounds on a surface. This may be useful for controlling tissue regeneration or other processes that are affected by the concentration of specific agents.

A significant advantage of a cold plasma treatment is that it affects all exposed surfaces, as opposed to "line of sight" plasma treatments or chemical surface treatments. Additionally, plasma treatment avoids problems, such as "wetting" and residues, associated with chemical treatments. Therefore, three dimensional objects may be treated after they are molded or otherwise fabricated, thus minimizing problems which may arise during processing of functionalized PHAs. A limitation of gas plasma is that it is not practical for powdery materials, or liquid suspensions, due to the low pressure conditions of the treatment.

Typical applications for gas plasma involve surface cleaning, surface modification, and polymer deposition. These processes use the same type of plasma, but differ in the effect on the surface. Cleaning processes are designed to remove all organic material from an inorganic material to produce an "atomically clean" surface. Surface modification of "etching" is used to selectively alter the surface properties of an article, while not affecting the bulk of the material. Polymer deposition is performed to introduce a uniform surface coating to an object by exposing a plasma activated surface to a polymerizable reagent. Surface modification procedures are expected to be most useful for the derivatization of PHAs.

Oxygen and ammonia gas plasmas can be employed to introduce new carboxylic or amino groups, respectively, into the polymer. It is believed that the oxygen plasma functions as an oxidant. These functional groups can be utilized as sites for the covalent attachment of bioactive agents. PHO films have been activated using a gas plasma treatment, and were subsequently derivatized by covalent attachment of bioactive agents (see Example 18 which follows).

In the biomedical field, cold gas plasma treatments are used to increase biocompatibility, enhance cell attachment, immobilize drugs, reduce allergic response, depyrogenate and sterilize materials or devices. Treatments can be tailored to meet the specific needs of the application.

5. Methods for Removing Pyrogens from the PHAs

The polymers can be purified to reduce pyrogen levels either before or after fabrication of the polymers into various physical forms, although it is preferable to purify the materials before fabrication. In the latex form, the polymer may be subjected to two or more treatments designed to reduce pyrogen levels. If necessary, the dry solid form can be reconstituted as a latex using the procedures described, for example, by Koosha, F. Ph.D. Dissertation, 1989, Univ. Nottingham, UK, *Diss. Abstr. Int. B* 51:1206 (1990). This can be preferred, particularly when it is desirable to obtain a PHA with very low levels of endotoxin in the polymer for a tissue engineering application. The PHA latex may be dried to yield a solid form if desired. Preferably, devices prepared from the PHAs have less than 1000 endotoxin units, more preferably, less than 100 endotoxin units, and most preferably, less than 20 endotoxin units.

In the case of a PHA latex, depyrogenation can involve treatment with an oxidizing agent. The oxidizing agent must be selected such that it does not significantly degrade or adversely alter the physical or chemical nature of the PHA. Preferably, the oxidizing agent has good solubility in aqueous solutions. A preferred oxidizing agent is hydrogen peroxide. The latex may contain particles of any size, although the particles are preferably nanoparticles and/or microparticles. The latex particles may be crystalline or amorphous, but are more preferably amorphous.

Solid forms of PHAs, such as powders, films, and pellets, may be depyrogenated by dissolving the PHA in a suitable organic solvent and then performing a suitable depyrogenation step. The resulting PHA solution may be depyrogentaged, for example, with an oxidizing agent. Preferably, the oxidizing agent has good solubility in the organic solvent used to dissolve the PHA, and does not significantly degrade or adversely alter the physical or chemical nature of the PHA. A preferred oxidizing agent is an organic peroxide. Particularly preferred oxidizing agents for use in organic solvents are aromatic peroxides such as benzoyl peroxide. Preferred solvents have good solubility for the specified PHA, and good stability for the oxidizing agent.

If necessary, the polymers can be depyrogenated by using combinations of the aqueous and organic-based oxidation treatments. A PHA latex, for example, may first be treated with hydrogen peroxide, and then subjected to a second treatment in an organic solution with an organic peroxide to further reduce endotoxin levels.

While it is generally preferred that a PHA is depyrogenated prior to fabrication of a tissue engineering scaffold or a stent, the methods described herein may also be applied in whole or in part to depyrogenate a fabricated PHA tissue engineering scaffold or a stent.

The use of oxidizing agents to reduce endotoxin levels in PHA polymers are preferred to the use of: physical treatments, such as heat and radiation, which can cause polymer degradation; other chemical treatments, such as hydrolysis and alkylation, which can modify the polymer structure; and, filtration and affinity techniques which are either unsuitable for depyrogenation of latex materials, or must overcome the high affinity of the PHA for endotoxin. However, these and other depyrogenation methods can be used to obtain the desired purity.

II. Methods for Manufacturing Medical Devices

The polymers are useful for preparing a variety of medical devices, including biodegradable implants. The biodegradable polymers preferably exhibit a relatively slow biodegradation, for example, having a in vivo half-life of between three and six months. The polymers preferably have a relatively low melting point/glass transition temperature, for example, less than 136° C., and/or are soluble in a non-toxic, non-halogenated solvent, for ease of processing.

When the depyrogenated PHAs are implanted in the body, these materials show very little, if any, acute inflammatory reaction or any adverse tissue reaction. There is no significant inflammatory response or scar tissue formation. Recruitment of inflammatory cells is minimal. Histological examination of the explanted devices demonstrates that the materials are essentially inert. Accordingly, devices constructed of PHAs can be implanted with minimal adverse affect on the surrounding tissue. Release of the hydroxy acid degradation products from the implanted materials typically is slow and well tolerated by the body. Thus, PHAs are expected to maintain their material properties for a matter of months and will eventually degrade to non-toxic materials.

Devices prepared from the PHAs can be used for a wide range of different medical applications. Examples of such applications include controlled release, drug delivery, tissue engineering scaffolds, cell encapsulation; targeted delivery, biocompatible coatings; biocompatible implants; guided tissue regeneration, wound dressings, orthopedic devices, prosthetics and bone cements (including adhesives and/or structural fillers), and diagnostics.

The PHAs can encapsulate, be mixed with, or be conically or covalently coupled to any of a variety of therapeutic, prophylactic or diagnostic agents. A wide variety of biologically active materials can be encapsulated or incorporated, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive compounds can be incorporated into a controlled release device. These include hydrophobic, hydrophilic, and high molecular weight macromolecules such as proteins. These bioactive compounds may either be covalently or non-covalently incorporated. The release profile may be adjusted by altering one or more of the following parameters: the nature of the PHA; the properties of the bioactive compound; the physical nature of the drug; and the nature of the device. The phrase "nature of the PHA" is used herein to mean, for example, the composition, structure, and molecular weight of the polymer or polymer mixture, including crosslinking and crystallinity. The phrase "properties of the compound" is used herein to mean, for example, the molecular weight, hydrophobicity and hydrophilicity. The phrase "physical nature of the compound" is used herein to mean, for example, the particle size and the loading of the compound. The bioactive compound can be incorporated into the PHAs in a percent loading of between 0.1% and 70% by weight, more preferably between 5% and 50% by weight. The phrase "nature of the device" refers to the device's physical shape, thickness, and form, which may be controlled by the fabrication technique.

PHAs may degrade over a period of as long as five years. Degradability is dependent on properties of the polyhydroxyalkanoate, such as the crystallinity and hydrophobilicty of the polymer, and the substitution of the polymer with groups which can promote hydrolysis (such as the copolymerization with polylactic acid, which can decrease degradation times substantially), as well as the form of the device. The PHAs may be in almost any physical form, such as a powder, film, molded item, particles, spheres, latexes, and crystalline or amorphous materials. They can be combined with additional non-PHA materials, for example, other polymers. They are suitable for use in applications requiring slowly degrading, biocompatible, moldable materials, for example, medical devices. Examples of medical devices which can be prepared from the polymers include rods, bone screws, pins, surgical sutures, stents, tissue engineering devices, and drug delivery devices, and wound dressings.

Degradable implants fabricated with the PHAs may be used in a wide range of orthopedic and vascular applications, tissue engineering, guided tissue regeneration, and applications currently served by other thermoplastic elastomers (McMillin, *Rubber Chem. Technol.*, 67:417-46 (1994)). The implants may include other factors to stimulate repair and healing. Preferred devices are tubes suitable for passage of bodily fluids. These devices may be modified with cell attachment factors, growth factors, peptides, and antibodies and their fragments.

1. General Methods of Preparing Medical Devices

Preferred methods of fabricating medical devices include solvent casting, melt processing, extrusion, injection and compression molding, and spray drying. Particles are preferably prepared directly from a fermentation based process, or by a solvent evaporation technique, double emulsion technique, or by microfluidization, using methods available in the art. (Koosha, F. Ph.D. Dissertation, 1989, Univ. Nottingham, UK., *Diss. Abstr. Int. B* 51:1206 (1990); Bruhn, B. W. and Müeller, B. W. *Proceed. Intern. Symp. Control. Rel. Bioact. Mater.* 18:668-69 (1991); Conti, B. et al. *J. Microencapsulation*, 9:153-166 (1992); Ogawa, Y. et al., *Chem. Pharm. Bull.,* 36:1095-103 (1988); Mathiowitz, E. and Langer, R. "Polyanhydride microspheres as drug delivery systems," M. Donbrow Ed., in "*Microcapsules Nanopart. Med. Pharm*." CRC, Boca Raton, Fla., 1992, Ch. 5, pp. 99-123.)

2. Methods for Fabricating Devices for Wound Healing

The PHAs can be fabricated into devices suitable for wound healing. For example, non-woven fibrous materials for this purpose may be prepared from the polymers by first producing polymer fibers, by pressing the polymers through a perforated outlet, using procedures known to those skilled in the art. The fibers can then be fabricated into a porous membrane (cloth) by spreading them on a solid support and subjecting them to compression molding. The thickness of the device is preferably less than 500 μm. The wound healing device may also be prepared by perforating a film or membrane using a laser to achieve porosity, or using a leaching technique to prepare a porous material. The pore sizes should ideally be small enough to lock out cells and other tissue matter. The wound healing devices may be positioned in vivo to separate tissues and stimulate tissue regeneration.

3. Method of Preparing Porous Membranes

Porous membranes including PHAs may be prepared a variety of methods known to those skilled in the art. For example, they may be prepared by solvent casting of polymer solutions containing leachable materials, and then leaching out the soluble inclusions from the polymers. Suitable leachable materials are simple non-toxic salts which dissolve readily in aqueous media. The porosity of the membranes may be controlled somewhat by selecting leachable materials with different particle sizes. After washing, and optionally sterilizing the resulting porous membranes, the membranes may be incubated in cell culture media and seeded with cells. Such materials may be used in tissue reconstruction.

4. Preparation of Nano or Microparticles

In one embodiment, nano or microparticles are prepared which encapsulate one or more agents to be delivered. The particles can be used to locally or systemically deliver a variety of therapeutic agents to an animal or can be used for diagnostic purposes. Particles fabricated from PHAs and which encapsulate antigens can be used for immunization. The preferred particles have particle sizes less than 50 μm, more preferably less than 10 μm, and are taken up by the Peyer's patches when administered orally, and are smaller if for injection. Preferred PHAs for this application are those which can be fabricated into vaccine devices without significantly reducing the immunogenicity of the antigen. Preferably, these devices increase the immunogenicity of the antigen.

5. Cellular Encapsulation

The PHAs may be used to encapsulate cells. Using procedures known to those skilled in the art, cells first may be pre-coated. Maysinger, *Reviews in the Neurosciences*, 6:15-33 (1995). Using a particle encapsulation procedure such as the double emulsion technique, the cells may then be encapsulated by PHAs. Ogawa, et al., *Chem. Pharm. Bull.*, 36:1095-103 (1988). Encapsulated cells may then be implanted in vivo.

6. Fabrication of PHA Tissue Engineering Scaffolds

The PHAs may be fabricated into tissue engineering scaffolds using a wide range of polymer processing techniques. Preferred methods of fabricating PHA tissue engineering scaffolds include solvent casting, melt processing, fiber processing/spinning/weaving, extrusion, injection and compression molding, lamination, and solvent leaching/solvent casting. Such methods are known to those skilled in the art.

One preferred method of fabricating a PHA tissue engineering scaffold involves using an extruder, such as a Brabender extruder. For example, this technique can be used to prepare extruded tubes suitable for implantation in a range of lengths and sizes.

Another preferred method involves preparing a nonwoven PHA scaffold from fibers. Fibers may be produced from the melt or solution, and processed into nonwovens using methods known to those skilled in the art. The properties of the nonwoven may be tailored by varying, for example, the PHA material, the fiber dimensions, fiber density, material thickness, fiber orientation, and method of fiber processing.

Another preferred method of preparing a PHA tissue engineering scaffold involves using a particulate-leaching technique for preparing a highly porous membrane. The technique involves dispersing particles in a solution of the PHA polymer, casting the PHA mixture into an appropriate mold, evaporating the solvent, and dissolving the particles out of the membrane. The properties, features and characteristics of the membrane may be varied considerably by altering, for example, the nature and size of the particles, applying and using different physical and chemical treatments during the fabrication, and varying the PHA type and solvents used. Suitable particles include salt crystals, proteins such as gelatin and agarose, starches, polysaccharides such as alginate and other polymers. The diameters of the particles may suitably be between nanometers to 500 microns. The porous membranes may, if desired, be further processed. For example, these membranes may be formed into hollow tubes.

As a variation on the particulate-leaching technique, the PHA scaffolds may be blended with particles, and melt processed into an appropriate mold. Particles may then be leached to yield suitable tissue engineering scaffolds.

Another preferred method involves melt or solvent processing a suitable PHA into an appropriate mold and perforating the material using a laser or other means to achieve the desired porosity. Also preferred are methods that include rolling a compression molded PHA sheet into a loop and heat sealing. The PHA sheet optionally may be rolled with another material, such as a second biodegradable polymer. For example, the latter material could be a nonwoven of polyglycolic acid, polylactic acid, or a copolymer of glycolic and lactic acids. Such a procedure should provide a laminated tube suitable for use in the engineering of new vessels, ducts and tubes.

The PHAs may also be used to coat other tissue engineering scaffolds. Such materials could be derived from other degradable polymers. Coating may be performed, for example, with a solvent based solution, or by melt techniques, or using a PHA latex.

The tissue engineering scaffold may also contain materials other than PHAs. These materials may alter, for example, physical and chemical properties. Such materials could include plasticizers, nucleating agents, and other polymers. Moreover, the scaffolds may be fabricated to contain bioactive compounds, detectable compounds and excipients. Examples of compounds that can be incorporated in PHA tissue engineering scaffolds include antiplatelet agents such as aspirin, dipyridamole, triclopidine, monoclonal antibody c7E3, Integrelin™, MK-852, MK-383, RO-44-9883; anti-thrombin agents such as heparin, low molecular weight heparin, R-hirudin, hirulog, argatroban, efegatran, Tick anticoagulant peptide, and Ppack; antiproliferative agents such as angiopeptin, ciprostene, calcium blockers, colchicine, cyclosporine, cytarabine, fusion proteins, Iloprost, ketaserine, prednisone, and trapidil; immunosuppressive agents; factors inhibiting ingrowth of fibrous tissue; factors inhibiting cancerous growth; oligonucleotides such as genes, DNA, and anti-sense sequences; radioactive compounds; growth factors; tissue inducing substances; proteins; peptides; antibodies and antibody fragments; biopharmaceuticals; and/or other active agents designed to promote, assist, and sustain tissue growth.

The tissue engineering devices described herein may be seeded with cells prior to implantation or after implantation. The cells may be harvested from a healthy section of the donor's tissue, expanded in vitro using cell culture techniques, and then seeded into a scaffold (or matrix) either prior to or after implantation. Alternatively, the cells may be obtained from other donor's tissue or from existing cell lines.

Examples of cells which can be seeded into tissue engineering scaffolds include hepatocytes, pancreatic cells, intestinal cells, uroendothelial cells, epithelial cells, skin cells (epidermal cells), muscle cells, nerve cells, mesenchymal cells, myocytes, chondrocytes, adipocytes, fibromyoblasts, ectodermal cells, and bone cells. The cells may be genetically engineered. The chosen cells are preferably dissociated, viable, and in suspension prior to application to the scaffold. In the case of scaffolds seeded prior to implantation, the cells should be provided with sufficient time to adhere to the polymer scaffold before being implanted. Alternatively, the PHA tissue engineering device may first be implanted, prevascularized, and then seeded with cells by, for example, injection.

The PHAs may be used in tissue engineering applications for virtually every tissue, including liver, cartilage, kidney, lung, skin, heart, bladder, pancreas, bone, uroepithelial-smooth muscle structures (especially ureters and urethras), tracheal epithelium, tendon, breast, arteries, veins, heart valves, gastrointestinal tubes, fallopian tubes, bile ducts, esophagus, and bronchi.

It may also be desirable to use the tissue engineering materials in conjunction with other therapies such as gene therapy, radiotherapy, and therapies requiring localization or delivery of an active agent. Tissue engineering may, for example, be used to deliver factors expressed by cells, which can if desired be genetically engineered, for the treatment of diseases.

7. Use of PHAs to Coat Devices

The PHAs may be used to coat other devices and materials. Such coatings may improve their properties for medical application, for example, improving their biocompability, mechanical properties, and tailoring their degradation and controlled release profiles. The PHAs may be coated onto other devices using the fabrication procedures described above. The thickness of the coating can be adjusted to the needs of the specific application by changing the coating weight or concentration applied, and/or by overcoating.

8. Fabrication of PHA Stents

The PHAs may be fabricated into stents using a wide range of polymer processing techniques. Preferred methods of fabricating PHA stents include solvent casting, melt processing, fiber processing/spinning, extrusion, injection molding, and compression molding. Such methods are known to those skilled in the art.

One preferred method of fabricating a stent involves extruding small tubes using, for example, a Brabender™ extruder. The tubes may be made in a range of lengths and sizes. Preferably the tubes should have smooth surfaces to provide good compatibility and fit against vessel walls. If desired the tubes may be perforated, for example, using a laser or by other means.

Another preferred method involves rolling a compression molded PHA sheet into a loop and heat sealing. The PHA sheet may optionally be rolled with another material, such as a second biodegradable polymer. The latter could, for example, be a polylactic acid mesh. Such a procedure provides a laminated stent.

The PHAs may also be used to coat existing stent materials. Such materials could be metallic, non-degradable polymers, or other non-PHA degradable polymers. Coating may be performed, for example, with a solvent based solution, or by melt techniques, or using a PHA latex.

The stent may also contain materials other than PHAs. These materials may alter, for example, physical and chemical properties. Such materials could include plasticizers, nucleating agents, and other polymers. Moreover, the devices may be fabricated to contain bioactive compounds, detectable compounds and excipients. Examples of compounds which may be included in PHA stents are antiplatelet agents such as aspirin, dipyridamole, triclopidine, monoclonal antibody c7E3, integrelin, MK-852, MK-383, RO-44-9883; antithrombin agents such as heparin, low molecular weight heparin, R-hirudin, hirulog, argatroban, efegatran, Tick anticoagulant peptide, and Ppack; antiproliferative agents such as angiopeptin, ciprostene, calcium blockers, colchicine, cyclosporine, cytarabine, fusion proteins, Iloprost, ketaserine, prednisone, and trapidil; radioactive compounds; and oligonucleotides such as genes and anti-sense sequences. In addition, the PHA stents also may contain cells, particularly genetically engineered cells, viruses, and other therapeutically beneficial components.

9. Targeting of PHA Particles and Devices

The PHAs may be modified for passive targeting after fabrication as devices or particles. Optionally, the particles may contain bioactive compounds or detectable substances. Preferred particle sizes are less than 100 µm, more preferably less than 15 µm. The particles may be further modified to improve targeting and prevent removal from the circulation by covalent or non-covalent incorporation of additional molecules. Examples of molecules which may be incorporated to improve targeting and prevent removal from the circulation are surface active agents, charged molecules, and PEG.

In addition to passive targeting, the PHAs may be actively targeted to a particular organ, group of cells within an organ, or site within a cell. Alternatively, an implant device prepared from low melting PHAs may actively attract bioactive substances, including cells. Using the procedures described for covalent modification of low melting PHAs and their derivatives, and those procedures described for fabrication of PHA devices, targeting molecules may be attached to the polymers. For example, targeting sequences such as peptides and proteins, such as antibodies and their fragments, may be coupled to carboxylic acids liberated by partial hydrolysis of the polymer backbone or present on the polymer's pendant groups. Other coupling chemistry, known to those skilled in the art, can be used to covalently attach these targeting sequences and others to different functional groups on the PHAs.

Preferred functional groups for attaching of targeting molecules to PHAs are carboxylic acids, amines, thiols, alcohols, unsaturated groups, and halogens. Preferred targeting molecules are cell attachment factors, antibodies, antibody fragments, and growth factors. The devices prepared from low melting PHAs containing active targeting molecules may be injected, implanted or delivered orally, and used, for example, in wound healing applications such as guided tissue regeneration, and chemotherapy.

10. Sterilization

Prior to implantation, a bioresorbable polymeric article must be sterilized to prevent disease and infection of the recipient. Sterilization is performed prior to seeding a polymeric device with cells. Heat sterilization of PHA containing articles is often impractical since the heat treatment could deform the article, especially if the PHA has a melting temperature below that required for the heat sterilization treatment. This problem can be overcome using cold ethylene oxide gas as a sterilizing agent. Exposure of a PHA containing article to vapors of ethylene oxide prior to implantation sterilizes the article making it suitable for implantation. During sterilization with cold ethylene oxide gas, the PHA containing article maintains its shape. This type of treatment is ideally suited for sterilization of molded, or pre-formed articles where the shape of the article plays in important role in its proper functioning.

Ethylene oxide vapors should also aid in the detoxification of pyrogen contaminants of a PITA containing article. As a powerful alkylating agent, ethylene oxide can detoxify pyrogens through an alkylation mechanism. This mechanism of detoxification is similar to that of acylation by an anhydride or mixed anhydride. For example, treatment of pyrogens or endotoxins with acetic anhydride or succinic anhydride is a well known method for detoxification and depyrogenation. The mechanism of action for detoxification of pyrogens by these anhydrides is believed to be conversion of the pyrogens to a non-toxic derivative via acylation. Ethylene oxide will behave in a similar manner via alkylation of the pyrogens.

III. Methods of Using Articles of Manufacture

The devices described herein can be administered systemically or locally, or even used in vitro, particularly for cell culture. The preferred methods of systemically administering the devices are by injection, inhalation, oral administration and implantation. Other suitable methods for administering the devices include administering the devices topically, as a lotion, ointment, patch, or dressing. The polymers can also be incorporated into chewing gums, a technique known to those skilled in the art. Rassing, *Adv. Drug Delivery Rev.*, 13:89-121 (1994). The PHAs devices prepared according to the above procedures can be used for a wide range of different medical applications.

The compositions and methods described herein will be further understood with reference to the following non-limiting examples.

EXAMPLE 1

Depyrogenation of a Copolymer Latex of
R-3-hydroxyoctanoic acid and R-3-hydroxyhexanoic acid with Hydrogen Peroxide A copolymer of R-3-hydroxyoctanoic acid and R-3-hydroxyhexanoic acid, derived by fermentation, containing over one million endotoxin units per gram (EU/gram), as measured with the copolymer in a latex form, was depyrogenated.

The latex was prepared by dissolving hexane-extracted PHA in acetone (1% wt/vol, 2.5 mL) and adding via flame-drawn pipet into 5 mL pyrogen-free water at 80° C. After 30 min at this temperature, the sample was divided into two equal portions: control and treated. To the treated sample was added 25 microliters 50% hydrogen peroxide and the sample was boiled for one hour. Both control and treated samples were assayed for endotoxin by the *Limulus* amebocyte lysate (LAL) test (Associates of Cape Cod, Mass.).

The endotoxin content of the polymer after treatment of the polymer was less than 6 EU/gram.

EXAMPLE 2

Depyrogenation of a Solid Copolymer of
R-3-hydroxyoctanoic acid and R-3-hydroxyhexanoic acid with Hydrogen Peroxide A copolymer of R-3-hydroxyoctanoic acid and R-3-hydroxyhexanoic acid, derived by fermentation, containing over one million EU/gram, as measured by the LAL test, was depyrogenated by treating the bulk polymer with aqueous hydrogen peroxide at 80° C. in a biphasic reaction.

The endotoxin content of the polymer after treatment of the polymer was 100 EU/gram, measured as a latex using the LAL test.

EXAMPLE 3

Depyrogenation of a Solid Copolymer of
R-3-hydroxyoctanoic acid and R-3-hydroxyhexanoic acid with Phthalic Anhydride A copolymer of R-3-hydroxyoctanoic acid and R-3-hydroxyhexanoic acid, derived by fermentation, containing over one million EU/gram measured by the LAL test, was depyrogenated by treating the bulk polymer with phthalic anhydride at 75° C.

The endotoxin content of the polymer after treatment was 500 EU/grain, measured as a latex using the LAL test.

EXAMPLE 4

Depyrogenation of a Solution of the Copolymer of
R-3-hydroxyoctanoic acid and R-3-hydroxyhexanoic acid with Potassium Permanganate A copolymer of R-3-hydroxyoctanoic acid and R-3-hydroxyhexanoic acid, derived by fermentation, containing over one million EU/gram measured by the LAL test, was depyrogenated by treating the polymer dissolved in dichloromethane with potassium permanganate.

The endotoxin content of the polymer after treatment of the polymer was 2500 EU/gram, measured as a latex using the LAL test.

EXAMPLE 5

Depyrogenation of a Solution of the Copolymer of
R-3-hydroxyoctanoic acid and R-3-hydroxyhexanoic acid with Sodium Hypochlorite A copolymer of R-3-hydroxyoctanoic acid and R-3-hydroxyhexanoic acid, derived by fermentation, containing over one million EU/gram measured by the LAL test, was depyrogenated by treating the polymer dissolved in dichloromethane with sodium hypochlorite.

The endotoxin content of the polymer after treatment of the polymer was 8000 EU/gram, measured as a latex using the LAL test.

EXAMPLE 6

Depyrogenation of a Solution of the Copolymer of
R-3-hydroxyoctanoic acid and R-3-hydroxyhexanoic acid with Basic Alumina A copolymer of R-3-hydroxyoetanoic acid and R-3-hydroxyhexanoic acid, derived by fermentation, containing over one million EU/gram measured by the LAL test, was depyrogenated by treating the polymer dissolved in dichloromethane with basic alumina.

The endotoxin content of the polymer after treatment of the polymer was 8000 EU/gram, measured as a latex using the LAL test.

EXAMPLE 7

Depyrogenation of a Solution of the Copolymer of
R-3-hydroxyoctanoic acid and R-3-hydroxyhexanoic acid with Benzoyl Peroxide A copolymer of R-3-hydroxyoctanoic acid and R-3-hydroxyhexanoic acid, derived by fermentation, containing over one million EU/gram measured by the LAL test, was depyrogenated by treating the polymer dissolved in dichloromethane with benzoyl peroxide. The PHA (0.25 g) was dissolved in dichloromethane (2.5 mL), to which was added benzoyl peroxide (50 mg) and stirred overnight at room temperature. The reaction mixture was then filtered through a cotton-plugges Pasteur pipette containing 2 g basic alumina to remove residual peroxide. The polymer was recovered from the filtrate by rotary evaporation and then prepared as an artificial latex and assayed for endotoxin.

The endotoxin content of the polymer after treatment of the polymer was 4000 EU/gram, measured as a latex using the LAL test.

EXAMPLE 8

Depyrogenation of Whole Cells Including a Copolymer of R-3-hydroxyoctanoic acid and R-3-hydroxyhexanoic acid with Hydrogen Peroxide A suspension of whole cells including a copolymer of R-3-hydroxyoctanoic acid and R-3-hydroxyhexanoic acid, derived by fermentation, containing over one million EU/gram measured by the LAL test, was depyrogenated by treatment with aqueous hydrogen peroxide (2% peroxide, 0.6% surfactant, 10% solids, pH 7, 80° C.) for 3.5 hours. After treatment, the composition was cooled, centrifuged, washed with an aqueous surfactant solution, water, precipitated, pelleted by centrifugation, and freeze dried. The endotoxin content of the treated polymer was 50 EU/gram, measured as a latex using the LAL test.

EXAMPLE 9

Depyrogenation of Whole Cells Including poly-R-3-hydroxybutyric acid with Hydrogen Peroxide A suspension of whole cells including poly-R-3-hydroxybutyric acid (PHB), derived by fermentation, was depyrogenated by treatment with aqueous hydrogen peroxide (2% peroxide, 0.6% surfactant, EDTA, 10% solids, pH 7, 80° C.) for 3.5 hours. After treatment, the composition was cooled, centrifuged, washed with an aqueous surfactant solution, water, precipitated, pellet by centrifugation, and freeze dried.

The endotoxin content of the treated polymer was less than 0.12 EU/gram, measured as a powder using the LAL test. By comparison the endotoxin content of a commercial sample of PHB was greater than 120 EU/gram measured as a powder.

EXAMPLE 10

Method for Preparing a High Purity Polyhydroxyalkanoate with a Melting Point below 136° C. Using Chloroform Extraction A copolymer of R-3-hydroxyoctanoic acid and R-3-hydroxyhexanoic acid with a melting point of 61° C., derived by fermentation of *Pseudomonas putida* KT2442, was extracted from freeze-dried cells with chloroform. The chloroform solution was filtered through a glass microfiber filter (2.7 µm) to remove particulates. The solution was concentrated, and the polymer precipitated via slow addition of a ten fold excess of methanol. The polymer was then dissolved in chloroform and cast as a film. The chloroform was allowed to evaporate completely, to yield a polymeric film.

EXAMPLE 11

Method for Preparing a High Purity Polyhydroxyalkanoate with a Melting Point Below 136° C. Using Hexane Extraction A copolymer of R-3-hydroxyoetanoic acid and R-3-hydroxyhexanoic acid with a melting point of 61° C., derived by fermentation of *Pseudomonas putida* KT2442, was extracted from freeze-dried cells with hexane. The hexane solution was filtered through a glass microfiber filter (2.7 µm) to remove particulates. The hexane was removed by distillation. The polymer was dissolved in acetone, and the polymer precipitated by addition of a ten fold excess of methanol. The polymer was collected, dissolved in acetone, and cast as a film. The acetone was allowed to evaporate completely to yield a polymeric film.

EXAMPLE 12

Method for Preparing a High Purity Polyhydroxyalkanoate with a Melting Point Below 136° C. Using Acetone Extraction A copolymer of R-3-hydroxyoetanoic acid and R-3-hydroxyhexanoic acid with a melting point of 61° C., derived by fermentation of *Pseudomonas putida* KT2442, was extracted from freeze-dried cells with acetone. The acetone solution was filtered through a glass microfiber filter (2.7 µm) to remove particulates. The acetone was removed by distillation. The polymer was dissolved in acetone, and polymer precipitated by addition of water. The polymer was collected using centrifugation to assist in the separation of phases, dissolved in acetone, and cast as a film. The acetone was allowed to evaporate completely to yield a polymeric film.

EXAMPLE 13

Method for Preparing a High Purity Polyhydroxyalkanoate Latex Particles with a Melting Point Below 136° C.

Whole cells containing a copolymer of R-3-hydroxyoctanoic acid and R-3-hydroxyhexanoic acid with a melting point of 61° C., derived by fermentation of *Pseudomonas putida* KT2442, were treated with 2% aqueous hydrogen peroxide, SDS (0.6%), pH 7, 80° C., for 3.5 hours. The latex was cooled, centrifuged and washed three times with a 0.4% SDS solution, and then washed two times with water.

EXAMPLE 14

Biocompatibility of a Polyhydroxyalkanoate Polymer Composition with a Melting Point Below 136° C.

A copolymer of R-3-hydroxyoctanoic acid and R-3-hydroxyhexanoic acid with a melting point of 61° C., derived by fermentation, was fabricated into devices and implanted subcutaneously in adult female mice. The implants were removed at 2, 4, 8, 12 and 40 weeks post-implantation and prepared for histological examination. Biocompatibility of the implants was evaluated by determining the degree of the fibrotic reaction surrounding the tissue samples and the presence of inflammatory cells.

Histological analysis showed minimal tissue reaction with no macrophages or histocytes present, suggesting that there were no signs of chronic inflammation or foreign body response to the polyhydroxyalkanoate.

EXAMPLE 15

In vivo Degradation of a Polyhydroxyalkanoate Polymer Composition with a Melting Point Below 136° C.

The molecular weight of the copolymer of Example 10 was determined prior to implantation, and after being implanted for 40 weeks. A control unimplanted sample was checked after 40 weeks. Molecular weight was determined by GPC.

The weight average molar mass, Mw, of the polymer prior to implantation was 137,000. After 40 weeks, although there were no visible signs of degradation or loss of mechanical properties, the Mw of the polymer was around 65,000. The number average molar mass, Mn, of the polymer prior to implantation was 58,000 compared to 31,000 after 40 weeks of implantation. Additional samples were taken from implants to compare the molecular weights at the surface versus the interior of the implants. No significant differences were observed, indicating a slow homogeneous hydrolytic breakdown of the polymer in vivo.

EXAMPLE 16

Controlled Release from a Device Prepared from Low Melting PHAs

Controlled release devices were fabricated from a copolymer of R-3-hydroxyoctanoic acid and R-3-hydroxyhexanoic acid with a melting point of 61° C. Model drug and polymer were co-dissolved in chloroform at 20% wt/vol total concentration and cast in small Petri dishes. After standing in air for several days, polymer films were obtained which contained the drug in dispersed form. Disks were then cut from each film sample using a 7/16" cork borer. The devices contained three different compounds, which (in order of increasing lipophilicity) were β-hydroxytheophylline, prednisolone-21-hemisuccinate, and lidocaine. Each drug was tested at three different loadings (4, 10, and 25% wt/wt). Each device, typically weighing around 85 mg, was deposited in a stoppered glass tube and immersed in 2 mL buffer comprising 100 mM sodium phosphate, pH 7.4, 0.02% sodium azide (sterile filtered) and maintained at 37° C. A control device containing polymer alone was included in the studies to monitor degradation of the polymer and release of impurities. At regular intervals, a sample was withdrawn and replaced with an equal volume of fresh buffer. Release of the compound was monitored by UV spectroscopy at the appropriate wavelengths (β-hydroxytheophylline [l=272 nm], prednisolone-21-hemisuccinate [l=252 nm], and lidocaine [l=262 nm]), and release values were normalized against the total quantity of drug released over the study period. For all the devices a significant amount of the compound was released in the first 24 hour period. After this, for both β-hydroxytheophylline and lidocaine, the percent of drug release on a daily basis was inversely proportional to the percentage of drug loading.

EXAMPLE 17

Chemical Modification of PHO Film

A PHO film was dotted with DMSO solutions of 5-(Biotinamido)-pentylamine (Pierce Chemical Col. product #212345) in a variety of organic co-solvents: isopropanol, acetonitrile, methanol, ethanol, and propylene carbonate. The biotin reagent contains a primary amino group attached to a penta-methylene linker. This amino group can cause aminolysis reactions with the polyester backbone of the PHA, resulting in scission of the polymer chain and covalent attachment of biotin. After biotinylation, the excess reagent was washed away and the amount of biotinylation was quantified using ELISA (enzyme linked immunosorbent assay) techniques with a streptavadin-horseradish peroxidase/chemiluminescence system. The strength of the signal, which is proportional to the amount of biotin, was dependent upon the co-solvent used and increased in the series: isopropanol greater than acetonitrile which is greater methanol, ethanol greater than propylene carbonate. Solvent controls were performed to demonstrate the dependence of the signal on the biotin reagent.

EXAMPLE 18

Gas Plasma Modification of PHO Film

PHO films were gas plasma treated in two different plasmas, ammonia and oxygen. These plasmas are expected to introduce new amino and carboxyl functional groups, respectively. These functional groups can act as sites for the covalent attachment of bio-active agents, such as a protein. Surface treatment was found to increase the water wettability of the PHO film compared with untreated PHO. This result is a strong indication of surface modification. Protein (rabbit IgG) was covalently coupled to the films using an aqueous solution of the protein and the coupling reagent EDC. The amount of coupled protein was quantified using a goat anti-rabbit antibody/horseradish peroxidase/chemiluminescence system. The strength of the signal was found to be proportional to the amount of rabbit IgG attached to the surface. Controls (-EDC, -rabbit IgG) were performed to demonstrate the dependence of the signal on these two components.

EXAMPLE 19

Tubular Tissue Engineering Devices

Tissue engineered tubular devices can serve a variety of functions for the replacement of tubular, biological tissues, such as vascular grafts, heart valves, urethra, intestines, nerve growth tubes, ducts, sphincter muscles, skin sheathes, etc. As PHAs are semi-crystalline, thermoplastic materials, a tubular PHA device can be formed in a variety of ways, such as extrusion, molding, pressing, and shaping or from solution using solution casting techniques. After forming the PHA into the desired shape and allowing the PHA to crystallize, a PHA article will maintain its shape for use as a tissue engineered article.

PHO was pressed into a thin film between two sheets of Mylar™. A Carver press at a platen temperature of 60° C. was used to supply 1 ton of pressure for 20 seconds. Spacers of appropriate thickness are used to control film thickness. The pressed film was placed in a refrigerator at 4° C. overnight to allow the PHO to crystallize. The PHO film was removed from the Mylar™ backing sheets and rolled into a tube shape on a cylindrical, Teflon™ support. The support diameter was chosen to produce a tube of a desired size and diameter. The film edges at the seam were sealed using compression, however, the seams may also be sealed via welding, melting, or partially dissolving the edges together. The tube was allowed to solidify prior to removal from the support.

EXAMPLE 20

Porous Tissue Engineering Devices

It is desirable to utilize a porous material for many tissue engineering applications. There are several advantages to using a porous material such as better diffusion of fluids and nutrients, increased surface area, increased cellular attachment, faster degradation, and greater tissue contact. For many tissue engineering applications, it is desired to utilize pores which are approximately 50 to 200 μm in diameter (for seeding of cells, preferred interstitial spacings on the order of 100 to 300 microns are not unusual), however, the optimum porosity, pore size and density of a porous material will vary depending upon its intended application. Pores can be introduced in a polymeric material using a variety of techniques such as foaming agents, processing of fibers into woven or non-woven structures, phase separation and leaching. Leaching strategies involve dispersing a solid material (such as salt) within the polymer. The solid material is chosen such that it is poorly soluble in the polymer and readily removed by leaching. The solid can be an inorganic or organic material, for example, a salt, sugar, protein, or polymer. After dispersing the solid in the polymer, the mixture can be formed into the desired shape. After constructing a device from the solid-polymer mixture, the solid is selectively dissolved away using a solvent in which the solid is soluble but in which the polymer is poorly soluble. The solid particles dissolve away to leave behind vacant pores. The size, distribution, and weight percent of the particles may be chosen to produce materials with a range of porosities.

A porous PHA tube was made. PHO was melted and mixed with sieved salt particles in a weight ratio of 1 to 2 to yield a homogeneous mixture. The salt particles used had been sieved between 80 and 180 μm, however the particle size, distribution and weight percent may be varied depending upon the desired pore size and density. The PHO/salt mixture was pressed into a thin film between two sheets of Mylar™. A Carver press at a platen temperature of 60° C. was used to supply 1 ton of pressure for 20 seconds. Spacers of appropriate thickness were used to control film thickness. The pressed film was placed in a refrigerator at 4° C. overnight to allow the PHO to crystallize. The PHO/salt film was removed from the Mylar™ backing sheets and rolled into a tube shape on a cylindrical, Teflon™ support. The support diameter was chosen to produce a tube of a desired size and diameter. The film edges at the seam were sealed using compression, however, the seams may also be sealed via welding, melting, or partially dissolving the edges together. The tube was allowed to solidify and was soaked in a water bath with frequent changes of the water to dissolve away the salt. After exhaustive leaching of the salt, a porous tube of PHO remained. The porous tube had properties which make it suitable for use as a vascular graft.

EXAMPLE 21

Construction of a PHA Heart Valve

Tissue engineered PHA devices can serve a variety of functions for the replacement of complex biological tissues, including valves, organs, and skeletal tissues. As PHAs are semi-crystalline, thermoplastic materials, a PHA device can be formed in a variety of ways such as extrusion, molding, pressing, and shaping or from solution using solution casting techniques. After forming the PHA into the desired shape and allowing the PHA to crystallize, a PHA article will maintain its shape for use as a device for tissue engineering.

A porous PHA heart valve was made. PHO was melted and mixed with salt particles in a weight ratio of 1 to 2 to yield a homogeneous mixture. The salt particles had been sieved between 80 and 180 μm, however, the particle size, distribution and weight percent may be varied depending upon the desired pore size and density. The PHO/salt mixture was pressed into a thin film between two sheets of Mylar™. A Carver press at a platen temperature of 60° C. was used to supply 1 ton of pressure for 20 seconds. Spacers of appropriate thickness were used to control film thickness. The pressed film was placed in a refrigerator at 4° C. overnight to allow the PHO to crystallize. The PHO/salt film was removed from the Mylar™ backing sheets. A PHO/salt film of approximately 250 μm thickness was used to form each of three valve leaflets. The leaflets were cut into the desired shape, which approximated that of biological leaflet. The leaflets were welded onto another PHO/salt film which served as a cylindrical conduit. The conduit film was 1 mm thick and made from a PHO/salt mixture of the same composition as the leaflets. Welding was performed using a heated probe at 50° C. to melt the PHO together at the seams. The leaflets were positioned using a natural heart valve as a model. The conduit was welded into the shape of a tube to complete the construction of the valve. The valve was allowed to solidify at 4° C. overnight. After exhaustive leaching of the salt in a water bath, a porous PHO heart valve remained. The valve leaflets had very good flexibility and the valve had very good handleability.

EXAMPLE 22

Cell Seeding of PHA Materials

Prior to implantation, tissue engineered materials may be seeded with cells to enhance their biocompatibility and/or to promote the growth of a desired tissue. The cells used are chosen from the appropriate type of tissue and are preferentially harvested from the patient to minimize tissue rejection, however, the cells may come from a cell bank. Additionally, bioactive compounds which direct the growth of a desired tissue, such as cell attachment proteins, can be incorporated onto or into a tissue engineered material prior to cell seeding and implantation. The tissue engineering material thus serves as a solid support to organize the cells for proper growth. After cell seeding, the cells can be grown in vitro on the tissues construct to reach the desired cell density.

A porous PHO sample was sterilized in ethylene oxide gas. The polymer was seeded with bovine endothelial cells in fetal bovine serum and then incubated in vitro at 37° C. with 5% carbon dioxide. After 24 hours, the cells were fixed onto the sample. Microscopic examination of the sample demonstrated good cellular attachment and biocompatibility.

EXAMPLE 23

Surface Modification of a PHA Film

The surface properties of a tissue engineering device are very important, since the surface is the interface between the host's living tissue and the implanted device. Surface modification can introduce new functionality to a polymer surface without significantly modifying the bulk properties of the polymer. Some surface properties which can be modified include hydrophobicity, hydrophilicity, wettability, cellular attachment, and surface charge. It is preferred to adjust the surface properties of a device to suit its intended application. For instance, often it is preferred to maximize cellular attachment to a device. In such a case, the surface of the device might be coated with a bioactive compound or peptide which promotes cellular attachment, such as fibronectin, laminin or gelatin. These bioactive compounds may be covalently or non-covalently attached to the surface, depending upon the application.

Gas plasma treatment was used to modify the surface of a PHA film. In order to prevent sample melting during treatment, conditions were designed to keep heating to a minimum. A PHO film was treated with an ammonia gas plasma, at 250 microns of ammonia with a flow of 350 SCCM with 220 watts of power for 10 minutes. Typically, plasma treatment covalently modifies a material's surface. After treatment, surface modification was confirmed by ESCA analysis. Stable incorporation of about 8% nitrogen was achieved. After treatment, samples were stored at 4° C. and RT. Surface wettability was determined by water contact angle measurements. Untreated PHO has a high contact angle (approximately 95°). After treatment the contact angle decreased dramatically to about 20 to 30°, demonstrating an increase in wettability. The contact angles of the treated and untreated samples were stable over at least 30 days, demonstrating stability of the surface modification. ESCA analysis was repeated after thirty days and confirmed stability of the surface modification.

EXAMPLE 24

Attachment of Bioactive Materials to PHA

A device used for tissue engineering may have incorporated inside of it or onto its surface a bioactive compound(s). Representative compounds include growth factors to stimulate tissue growth, cellular attachment proteins to promote tissue attachment, or anti-coagulants to prevent thrombogenesis. Additionally, compounds may be included which reduce the immune response, label the material for later retrieval, enhance biocompatibility, deliver drugs or the like.

A bioactive compound was attached to a PHA surface, as follows. A PHO film was modified with a biologically active compound, biotin, after ammonia gas plasma treatment. An aqueous solution containing an activated form of biotin was applied to the treated PRO film. The biotin derivative contained an N-hydroxysuccinimide ester functional group which activated it for acylation. After treatment with biotin-NHS, the film surface was washed with water, quenched with glycine and blocked with 0.1% gelatin. Detection with a streptavidin horseradish peroxidase conjugate and a chemi-luminescent HRP detection solution demonstrated biotin modification of the surface. A PHO film without ammonia gas plasma treatment was used as a control and demonstrated no biotin modification under identical conditions.

EXAMPLE 25

Testing of a Hypoallergenic Latex

A 60 cm² sample of PHO was assayed for skin sensitization according to standard test method ASTM F720. The sample, 3 mm in thickness, was extracted with saline at 50° C. for 72 hr (20 ml). Guinea pigs, previously subjected to two-stage induction (21 days) were exposed on the skin to patches soaked in the saline extract, pure saline, or a positive control solution (5% oxazolone in acetone). After 24 hrs, the patches were removed, and the guinea pigs were checked for a skin reaction after 1, 24 and 48 hours. There was no discernible erythema/eschar formation with the PHO extract or the pure saline; positive controls all showed well-defined to severe erythema/eschar formation within one hour.

Those skilled in the art will recognize, or be able to ascertain using no more than routine experimentation, many equivalents to the specific embodiments of the invention described herein. Such equivalents are intended to be encompassed by the following claims.

We claim:

1. A biocompatible medical device comprising a polyhydroxyalkanoate polymer which is prepared using a process which introduces a pyrogen into the polyhydroxyalkanoate, wherein the pyrogen is removed from the polyhydroxyalkanoate using an oxidizing agent under conditions effective to produce a pyrogen level of less than 20 endotoxin units (EU) per device.

2. The device of claim 1 wherein the device is in a form selected from the group consisting of stents, coatings on prosthetic devices, sutures, staples, and tubing.

3. The device of claim 1 wherein the device is in a form selected from the group consisting of tissue regeneration devices, cell culture devices, vascular grafts, wound dressings, and cell or tissue coatings.

4. The device of claim 1 wherein the device is in a form selected from the group consisting of drug, diagnostic or prophylactic delivery devices.

5. The device of claim 1 wherein the device is a porous membrane.

6. The device of claim 1 wherein the device comprises a material selected from the group consisting of therapeutic, prophylactic and diagnostic agents.

7. The device of claim 6 wherein the device comprises a therapeutic agent selected from the group consisting of peptides, proteins, nucleic acids, saccharides, polysaccharides, lipids, synthetic drug molecules, and imaging agents.

8. The device claim 1 wherein the device is formulated for administration to a mucosal surface.

9. The device of claim 1 wherein the polyhydroxyalkanoate is a homopolymer, polymer blend or copolymer.

10. The device of claim 1 wherein molecules are bound to the polymer, and the molecules are selected from the group consisting of molecules which are bioactive, molecules which can be detected, targeting molecules, and molecules affecting charge, lipophilicity or hydrophilicity of the polymer.

11. The device of claim 1 wherein the device is for tissue engineering further comprising cells seeded onto or within the device.

12. The device of claim 1 wherein the device is formed into a bone prosthesis.

13. The device of claim 1 further comprising structural and adhesive materials to form a bone cement.

14. The device of claim 1 in the form of a heart prosthetic selected from the group consisting of heart valves, heart leaflets, and heart anulus.

15. The device of claim 1 in the form of a periodontal graft.

16. The device of claim 1 in the form of a pericardial patch.

* * * * *